United States Patent [19]

Schmid et al.

[11] Patent Number: 4,622,303

[45] Date of Patent: Nov. 11, 1986

[54] DEFOAMERS FOR YEAST FERMENTATION

[75] Inventors: Karl Schmid, Mettmann; Joachim Schindler, Hilden; Adolf Asbeck, Duesseldorf, all of Fed. Rep. of Germany

[73] Assignee: Henkel Kommanditgesellschaft auf Aktien, Duesseldorf, Fed. Rep. of Germany

[21] Appl. No.: 695,763

[22] Filed: Jan. 29, 1985

[30] Foreign Application Priority Data

Sep. 24, 1984 [DE] Fed. Rep. of Germany ....... 3434984

[51] Int. Cl.$^4$ .......................... C12N 1/00; C12N 1/16; B01D 17/00
[52] U.S. Cl. .................................... 435/243; 435/246; 435/255; 435/812; 435/240; 435/3; 252/321; 252/358; 514/937; 514/943; 514/945
[58] Field of Search .............. 435/812, 255, 243, 246, 435/240, 3; 252/321, 358; 514/937, 943, 945

[56] References Cited

U.S. PATENT DOCUMENTS

| | | | |
|---|---|---|---|
| 2,759,871 | 8/1956 | Cash | 435/812 |
| 3,784,479 | 1/1974 | Keil | 242/358 |
| 3,920,559 | 11/1975 | Elting | 252/8.5 |
| 4,280,919 | 7/1981 | Stoeckigt et al. | 252/135 |
| 4,522,740 | 6/1985 | Schmid et al. | 252/321 |

FOREIGN PATENT DOCUMENTS

| | | | |
|---|---|---|---|
| 19173 | of 0000 | European Pat. Off. | |
| 97786 | of 0000 | European Pat. Off. | |
| 2161772 | 12/1971 | Fed. Rep. of Germany | 252/321 |
| 2410155 | of 0000 | Fed. Rep. of Germany | |
| 2074419 | of 0000 | France | |
| 4927751 | 7/1974 | Japan | |
| 775483 | of 0000 | United Kingdom | |
| 1336428 | of 0000 | United Kingdom | |
| 1489484 | of 0000 | United Kingdom | |

OTHER PUBLICATIONS

C.A. No. 188289q, vol. 95 (1979), Water Soluble Antifoaming Agents.
C.A. No. 86117u, vol. 94 (1980), Foam Suppressor, Basona et al.
C.A. No. 171889y, vol. 81, Composition for Foam Prevention in Aqueous Systems, Hedtrich et al.
C.A. No. 193365v, vol. 94 (1981), Antifoaming Agents.
European Search Report-EP 84 11 4864.

*Primary Examiner*—John Kight
*Assistant Examiner*—Garnette D. Draper
*Attorney, Agent, or Firm*—Ernest G. Szoke; Henry E. Millson, Jr.

[57] ABSTRACT

Troublesome foaming in the fermentation of yeast is suppressed by the addition of polyglycol ethers which are derived from saturated and monounsaturated $C_{16}$–$C_{18}$ fatty alcohols and which contain on an average of from 1 to 4 ethylene and/or propylene glycol ether groups. Preferred defoamers contain oleyl and cetyl alcohol residues in a ratio of from 3:1 to 1:1, and on average 2 ethylene glycol ether groups. The defoamers do not inhibit yeast growth or lead to premature softening and liquefaction of the compressed yeast.

12 Claims, No Drawings

DEFOAMERS FOR YEAST FERMENTATION

BACKGROUND OF THE INVENTION

1. Field of the Invention

The present invention relates to compounds for the suppression of foaming in yeast fermentation without the inhibition of yeast growth or the premature softening or liquefaction of the yeast when compressed.

2. Description of Related Art

It is known that yeasts, particularly baker's yeast, are industrially produced by the fermentation of molasses. Troublesome foaming can occur to a considerable extent during the fermentation process, particularly where it is carried out in modern, high-output fermentation plants. This foaming has to be suppressed by the addition of defoamers.

Now, in recent years, yeast manufacturers have complained that baker's yeast changes its consistency in storage, ultimately becoming soft or even liquid and hence unsaleable. The reduced yeast quality is blamed by the yeast industry on the increasing surfactant content of the molasses.

It has now been found that the consistency of baker's yeast is influenced by the nature of the foam inhibitor and that all the yeast defoamers hitherto available on the market or proposed for this purpose lead to more or less rapid softening of the yeast.

Accordingly, there is a considerable need for a defoamer which, even in small quantities, prevents troublesome foaming during the fermentation of yeast, has very little inhibiting effect on the growth of the yeast cultures and does not result in softening or liquefaction of the final yeast over a reasonable period of storage. This problem is solved by the present invention.

DESCRIPTION OF THE INVENTION

The present invention relates to the use of polyglycol ethers of linear, primary, saturated and mono-unsaturated $C_{16}$–$C_{18}$ alcohols containing ethylene glycol ether groups and/or propylene glycol ether groups as defoamers in the fermentation of yeast.

The polyglycol ethers used in accordance with the invention are derived from fatty alcohols of natural or synthetic origin containing from 16 to 18 carbon atoms, and preferably from mixtures of oleyl alcohol and cetyl alcohol. Although myristyl and stearyl alcohol can also be present in admixture with oleyl alcohol and cetyl alcohol, their quantity should not exceed 10% by weight in either case. Polyglycol ethers in which from about 30 to about 80% of the alcohol component consists of oleyl alcohol are particularly suitable. More highly unsaturated alcohols are unsuitable and should preferably be absent.

The number of polyglycol ether groups amounts on average to from 1 to 4 and preferably to from 1 to 3. As normal with commercial alkoxylation products, this figure represents a statistical average, i.e. the alkoxylation products may also contain small amounts of alcohols alkoxylated to a higher or lower degree, including unsubstituted alcohols, corresponding to a statistical distribution. The glycol ether groups can consist of ethylene glycol ether groups (EO) or propylene glycol ether groups (PO) or both. They preferably consist of EO-groups; their number amounting on average to from 1 to 3.

Polyglycol ethers derived from mixtures of oleyl alcohol and cetyl alcohol in a ratio by weight of from about 3:1 to about 1:1 and containing on average 2 EO-groups have proved to be particularly effective.

The present invention also relates to a process for defoaming aqueous yeast fermentation broths which is characterized in that from about 0.005 to about 1 g/l of polyglycol ethers of the type described above is added to the fermentation broth. The quantities added preferably amount to between about 0.01 and about 0.2 g/l.

The defoamers used in accordance with the invention are superior to all the products hitherto known and, in particular, were specially developed for use in fermentation broths to produce optimal defoaming activity, minimal growth inhibition, and high resistance of the treated yeasts to softening and liquefaction. Even an overdosage of 10 times the quantity required for adequate foam inhibition does not produce any significant adverse effects.

The invention will be illustrated by the following examples, which are given for that purpose only.

EXAMPLES

The following products were tested as defoamers:

I = $C_{16}$–$C_{18}$ fatty alcohol + 2 EO (35% cetyl, 60% oleyl, 5% stearyl alcohol)

II = $C_{16}$–$C_{18}$ fatty alcohol + 3 EO (same alcohol) base as I)

III = $C_{16}$–$C_{18}$ fatty alcohol + 1 PO (same alcohol base as I)

The following known defoamers were used for comparison (the abbreviation M stands for molecular weight).

$C_1$ oleic acid + 1.2 EO
$C_2$ oleic acid methyl ester
$C_3$ glycerin monooleate
$C_4$ castor oil + 5.5 EO
$C_5$ polypropylene glycol (M = 2020)
$C_6$ polypropylene glycol (M = 3800) + 22% by weight EO
$C_7$ saturated $C_{12}$–$C_{18}$ fatty alcohol + 2 EO + 4 PO
$C_8$ saturated $C_{12}$–$C_{18}$ fatty alcohol + 5 EO + 13 PO
$C_9$ saturated $C_{12}$–$C_{18}$ fatty alcohol + 14 EO + 54 PO
$C_{10}$ saturated $C_{12}$–$C_{18}$ fatty alcohol + 2 EO
$C_{11}$ oleyl alcohol (95%) + linoleyl alcohol (5%) + 2 EO
$C_{12}$ commercial fermentation defoamer A
$C_{13}$ commercial fermentation defoamer B The commercial defoamers used are the products Struktol® J 673 (A) and Struktol® KG 11 II (B) of Schill & Seilacher, Hamburg.

The tests were carried out in fermentation vessels in which finely dispersed air was introduced near the base. The fermentation broths consisted of dilute molasses inoculated with a commercial baker's yeast strain of the genus *Saccharomyces cerevisiae* and contained the usual growth promoters and additives. In each test, the defoamer was added in such a quantity that no continuous foam blanket could form. In addition, the growth inhibition produced by the addition of 0.1% and 1% by weight of defoamer was evaluated. The strength of the compressed yeast obtained as a function of the storage time (storage at 25° C.) was also determined. The results are shown in the following Table.

In the "growth inhibition" column, − means no inhibition, (−) slight inhibition and + pronounced inhibition.

| Product | Dosage g/l | Growth inhibition 0.1% | Growth inhibition 1% | Softening after ... days |
| --- | --- | --- | --- | --- |
| I | 0.02 | − | − | 28 |
| II | 0.3 | − | − | 13 |
| III | 0.07 | − | − | 20 |
| $C_1$ | 0.59 | − | − | 5 |
| $C_2$ | 0.05 | − | (−) | immediate |
| $C_3$ | 0.59 | − | + | 8 |
| $C_4$ | 0.11 | + | + | immediate |
| $C_5$ | 0.27 | − | − | immediate |
| $C_6$ | 0.07 | − | − | immediate |
| $C_7$ | 0.61 | − | − | 11 |
| $C_8$ | 0.41 | + | + | immediate |
| $C_9$ | 0.22 | + | + | 20 |
| $C_{10}$ | 0.46 | − | + | immediate |
| $C_{11}$ | 1.1 | + | + | 14 |
| $C_{12}$ | 0.5 | − | (−) | 10 |
| $C_{13}$ | 0.8 | − | − | 3 |

In the case of products $C_1$, $C_3$, $C_7$, $C_{12}$ and $C_{13}$, no growth inhibition and average resistance to softening of the compact yeast were observed, although the necessary in-use concentrations were relatively high. The remaining comparison products produced growth inhibition and/or immediate softening or liquefaction of the compressed yeast.

A leading position is occupied by product I which, even in a concentration of 0.02 g/l, suppressed troublesome foaming, did not inhibit growth and led to particularly stable compressed yeasts. Even in a 10-fold overdosage (0.2 g/l), this product did not produce any adverse effects. Although that quantity resulted in softening of the yeast after 21 days, this result is quite acceptable.

What is claimed is:

1. A method for defoaming an aqueous yeast fermentation broth comprising adding to such broth an effective quantity of polyglycol ethers of linear, primary, saturated and unsaturated $C_{16-18}$ alcohols containing an average of from 1 to 4 glycol ether groups which are ethylene glycol ether groups, propylene glycol ether groups, or a mixture of ethylene glycol ether and propylene glycol ether groups and wherein said polyglycol ethers contain from about 30 to about 80% by weight of oleyl alcohol component as the alcohol component.

2. A method in accordance with claim 1 wherein the polyglycol ethers contain an average of from 1 to 3 ethylene glycol ether groups.

3. A method in accordance with claim 2 wherein the polyglycol ethers contain an average of from 1 to 3 ethylene glycol ether groups.

4. A method in accordance with claim 1 wherein from about 0.005 to about 1 g/l of said polyglycol ethers are added to the fermentation broth.

5. A method in accordance with claim 4 wherein from about 0.01 to about 0.2 g/l of said polyglycol ethers are added to the fermentation broth.

6. A method in accordance with claim 1 wherein the alcohol component of the polyglycol ethers is a mixture of oleyl alcohol and cetyl alcohol components in a ratio by weight of from about 3:1 to about 1:1, and wherein the polyglycol ethers contain an average of 2 ethylene glycol ether groups.

7. A yeast fermentation broth which contains an effective foam inhibiting quantity of polyglycol ethers of linear, primary, saturated and unsaturated $C_{16-18}$ alcohols containing an average of from 1 to 4 glycol ether groups which are ethylene glycol ether groups, propylene glycol ether groups, or a mixture of ethylene glycol ether and propylene glycol ether groups and wherein said polyglycol ethers contain from about 30 to about 80% by weight of oleyl alcohol component as the alcohol component.

8. A fermentation broth in accordance with claim 7 wherein the polyglycol ethers contain an average of from 1 to 3 ethylene glycol ether groups.

9. A fermentation broth in accordance with claim 8 wherein the polyglycol ethers contain an average of from 1 to 3 ethylene glycol ether groups.

10. A fermentation broth in accordance with claim 7 wherein from about 0.005 to about 1 g/l of said polyglycol ethers are present in the fermentation broth.

11. A fermentation broth in accordance with claim 10 wherein from about 0.01 to about 0.2 g/l of said polyglycol ethers are present in the fermentation broth.

12. A fermentation broth in accordance with claim 7 wherein the alcohol component of the polyglycol ethers is a mixture of oleyl alcohol and cetyl alcohol components in a ratio by weight of from about 3:1 to about 1:1, and wherein the polyglycol ethers contain an average of 2 ethylene glycol ether groups.

* * * * *